(12) United States Patent
Baudin-Creuza et al.

(10) Patent No.: US 9,494,603 B2
(45) Date of Patent: Nov. 15, 2016

(54) METHOD FOR DIAGNOSING A HEMOGLOBIN-RELATED DISORDER

(71) Applicants: Veronique Baudin-Creuza, Le Kremlin-Bicetre (FR); Corinne Vasseur, Le Kremlin-Bicetre (FR); Frederic Galacteros, Creteil (FR)

(72) Inventors: Veronique Baudin-Creuza, Le Kremlin-Bicetre (FR); Corinne Vasseur, Le Kremlin-Bicetre (FR); Frederic Galacteros, Creteil (FR)

(73) Assignees: Institut National de la Santé et de la Recherche Médicale (INSERM), Paris (FR); Université Paris-Sud, Orsay (FR); Assistance Publique—Hopitaux de Paris, Paris (FR); Universite Paris Est Creteil Val de Marne, Creteil (FR)

( * ) Notice: Subject to any disclaimer, the term of this patent is extended or adjusted under 35 U.S.C. 154(b) by 0 days.

(21) Appl. No.: 14/748,894

(22) Filed: Jun. 24, 2015

(65) Prior Publication Data

US 2015/0293126 A1    Oct. 15, 2015

Related U.S. Application Data

(62) Division of application No. 13/265,898, filed as application No. PCT/EP2010/055479 on Apr. 23, 2010, now Pat. No. 9,097,728.

(30) Foreign Application Priority Data

Apr. 24, 2009  (EP) .................................. 09305352

(51) Int. Cl.
  *G01N 33/53*   (2006.01)
  *G01N 33/72*   (2006.01)

(52) U.S. Cl.
  CPC ............ *G01N 33/721* (2013.01); *G01N 33/53* (2013.01); *G01N 2800/22* (2013.01); *G01N 2800/52* (2013.01); *G01N 2800/56* (2013.01)

(58) Field of Classification Search
  CPC .............. G01N 33/721; G01N 33/53; G01N 2800/56; G01N 2800/22; G01N 2800/52
  See application file for complete search history.

(56) References Cited

U.S. PATENT DOCUMENTS

2005/0028229 A1*  2/2005  Weiss et al. ................ 800/18

FOREIGN PATENT DOCUMENTS

WO      2005/029092         3/2005
WO   WO 2005/029092    *   3/2005  ............ G01N 33/72
WO      2005/093413        10/2005

OTHER PUBLICATIONS

Gell et al. Biophysical Characterization of the α-Globin Binding Protein α-Hemoglobin Stabilizing Protein, The Journal of Biological Chemistry 277 (43): 40602-10609 (Oct. 25, 2002).*
Gell, David et al.; "Biophysical Characterization of the Alpha-Globin Binding Protein Alph-Hemoglobin Stabilizing Protein"; Journal of Biological Chemistry, American Society for Biochemistry and Molecular Biology, vol. 277, No. 43, Oct. 25, 2002, pp. 40602-40609.
Garver, Fred A. et al.; "Identification and Quantification of Hemoglobins A2 and Barts with an Enzyme-Labeled Immunosorbent Assay"; Clinical Chemistry, vol. 30, No. 7, 1984, pp. 1205-1208.
Kihm et al.; "An Abundant Erythroid Protein that Stabilizes free Alpha-Haemoglobin"; Nature 417: 758-763, Jun. 13, 2002.

* cited by examiner

*Primary Examiner* — Gail R Gabel
(74) *Attorney, Agent, or Firm* — Whitham, Curtis & Cook, P.C.

(57) ABSTRACT

The invention relates to a method for diagnosing, staging and/or monitoring a hemoglobin-related disorder such as β-thalassemia or a treatment against said hemoglobin-related disorder in a subject in need thereof based on the detection and/or quantification the presence of free α-Hb pool in a biological sample obtained from said subject.

10 Claims, 5 Drawing Sheets

METHOD FOR DIAGNOSING A HEMOGLOBIN-RELATED DISORDER

CROSS REFERENCE TO RELATED APPLICATIONS

This application is a Divisional Application based on U.S. Pat. No. 9,097,728 filed Oct. 24, 2011 which is a National Stage Application based on PCT/EP2010/055479 filed Apr. 23, 2010 which claims priority to European Application 09305352.8 filed Apr. 24, 2009.

FIELD OF THE INVENTION

The invention relates to a method for diagnosing and/or staging a hemoglobin-related disorder, such as β-thalassemias, in a subject in need thereof.

The invention also relates a method for monitoring a treatment against said hemoglobin-related disorder in a subject in need thereof.

BACKGROUND OF THE INVENTION

The normal development of red blood cells requires a coordinated synthesis of the hemoglobin (Hb) subunits, the α- and β-globins in the case of adult hemoglobin (Hb A). The α- and β-globin chains are encoded by genes on different chromosomes, 16 and 11 respectively, and their expression is controlled independently. In the normal red blood cell, slightly more α-chains than β-chains are produced. Unlike the β-hemoglobin chains (β-Hb) which are soluble and form homologous tetramers, the free α-hemoglobin chains (α-Hb) are highly instable, and when in excess, form precipitates and act as active oxidants causing apoptosis and inefficient erythropoiesis.

β-thalassemias are inherited autosomal recessive diseases characterised by a decrease or abolition of the normal β-globin chain synthesis inducing inefficient erythropoiesis (Weatherall, 2004). Consequences include anemia, of different severity according to the mutations involved, several other severe disorders due to the increase in medullar erythropoiesis, impaired statural growth and bone structure, accelerated iron turnover, and heme catabolism, and their own clinical consequences.

In 2002, the molecular chaperone of α-Hb, the <<Alpha-Hemoglobin Stabilizing Protein>> (AHSP) was reported (Kihm et al., 2002). This small protein of 102 amino-acids is present at a high level (0.1 mM) in human red blood cell precursors and its synthesis is under the control of GATA-1, a pivotal erythroid transcription factor. This protein is encoded by chromosome 16. Also, in contrast to most other molecular chaperones, which are widely expressed and relatively promiscuous with respect to substrate interactions, AHSP appears to be highly tissue and substrate specific. AHSP specifically binds to α-Hb to form a stable soluble heterodimer but not to the β-Hb or to tetrameric Hb A (Kihm et al., 2002; Gell et al., 2002). Hence the role of AHSP could be to prevent free α-Hb from aggregation until the encounter of β, δ or γ chains allows formation of the corresponding tetrameric Hbs. In the red blood cell of β-thalassemic patients, AHSP acts as a scavenger against the pool of free α-chain but may be overwhelmed by a defective production or level of availability of β-like chains. Thus, the free α-Hb monomers in the red cells overload the AHSP capacity and precipitate, damaging the cell and triggering cell apoptose. For β-thalassemic patients, the free α-chain pool in the red blood cell may thus reflect the severity of a β-thalassemia syndrome.

Based on AHSP identification, US Patent Application 2005/0028229 describes a method of diagnosing an AHSP-related disorder in a test subject such as β-thalassemia by determining the presence in a sample from said test subject of AHSP and, if present, determining the expression level.

However, currently the diagnosis of β-thalassemia is still based on the hematological parameters of the patients and the molecular diagnosis is obtained by PCR techniques. More than 200 different β-thalassemia mutations have now been characterized, the majority of which are point mutations or very short deletions/insertions. Most of these mutations are country or population-specific, and their distributions have now been determined for most at-risk populations. The strategy for identifying these mutations is usually based on the fact that most populations have just a few common mutations and a variable number of rare ones. The severity of the β-thalassemia depends mainly on the nature of the mutation. Two main classes of disorders are described, first the $β^0$-thalassemia ($β^0$-thal) in which no β chains are produced and second the $β^+$-thalassemia ($β^+$-thal) in which some normal β chains are synthesized. The clinical manifestations of β-thalassemia are extremely diverse ranging from severe anemia and transfusion-dependency to the asymptomatic state of β-thalassemia trait (Thein, 2005). More generally one may need to consider the overall imbalance between the α and β family of globin chains, in order to include the different stages of development; for example, the .beta. family includes the fetal (γ) and adult (β) chains. The great variability in the phenotypic expression of the .beta.-thalassemia also depends on association with some modifiers of Hb synthesis which may modify the .alpha. biosynthetic ratio between cluster β and α-globin.

Thus, the central pathological mechanism of β-thalassemias is the imbalance between the synthesis of the alpha and beta (γ+β) family of globin chains (Weatherall and Clegg, 2001) and the severity of this disease is directly correlated with the degree of the globin chain imbalance. The in vitro study of synthesis of the α- and γ+β-globin chains of Hb from peripheral blood reticulocytes highlighted in 1965 this imbalance of globin synthesis in thalassemia (Weatherall et al., 1965). Many subsequent studies have reported the same usefulness of measuring the imbalance of globin chain synthesis from β-thalassemic reticulocytes, but all the different laboratory methods are based on the incorporation of a radioactive amino acid in the subunit biosynthesis from peripheral blood (Kim et al., 1977). Such a method could certainly not be considered as routine laboratory practice.

It results that there is currently no simple and rapid test to evaluate this parameter. In routine hematologic examinations, the excess of free α-Hb may be distinguished in cytology by the presence of inclusion bodies corresponding to the denatured and precipitated α-Hb but this approach is not specific of the α-Hb and only qualitative. It is cumbersome, expensive and time consuming procedure.

Indeed, the only technique to quantify the relative excess of free α-Hb is to carry out globin biosynthesis in vitro in the presence of a radioactive amino-acid. This technology has been used in research laboratories in the 1970s, 1980s and the measurement of the amount of radioactivity in different collected globin fractions allows a determination of the α/β chain synthesis ratio. This characterization method is less and less in use, even in research laboratories, because of the use of radioactivity.

Furthermore, until very recently, it was considered that was impossible to detect or quantify free α-Hb since the excess α-Hb either precipitates in erythroid precursors in the bone marrow (resulting in ineffective erythropoiesis), causing their premature destruction, and although partly proteolyzed binds to the cell membrane of adult erythroid cells, leading to their hemolysis and promoting apoptosis (Bank, 2007 and Yu et al., 2007).

Therefore, there is a need for a method for easily diagnosing and/or staging a hemoglobin-related disorder such as β-thalassemias carried out without using molecular or radioactive technique.

SUMMARY OF THE INVENTION

The invention relates to a method for diagnosing and/or staging a hemoglobin-related disorder in a subject in need thereof, said method comprising:
  contacting a biological sample obtained from said subject with an alpha hemoglobin (α-Hb)-specific binding partner selected from the group consisting of Alpha-Hemoglobin Stabilizing Protein (AHSP) and beta hemoglobin (β-Hb),
  detecting and/or quantifying the presence of free α-Hb in said biological sample, and
  correlating said amount of free α-Hb with the diagnosis and/or the staging of a hemoglobin-related disorder in said subject.

The invention also relates to a method for monitoring a treatment against a hemoglobin-related disorder in a subject in need thereof, said method comprising:
  contacting a biological sample obtained from said subject with an alpha hemoglobin (α-Hb)-specific binding partner selected from the group consisting of Alpha-Hemoglobin Stabilizing Protein (AHSP) and beta hemoglobin (β-Hb),
  detecting and/or quantifying the presence of free α-Hb in said biological sample, and
  correlating said amount of free α-Hb with monitoring of a treatment against said hemoglobin-related disorder in said subject.

DETAILED DESCRIPTION OF THE INVENTION

The inventors made the observation that it is possible to detect and quantify the free α-Hb in a blood sample. This observation led them to find that such detection and quantification are useful for diagnosing, staging and/or monitoring a hemoglobin-related disorder in a subject in need thereof since it was shown that higher is the value of the free α-Hb pool, more the hemoglobin disorder is severe. It should be further noted that the method according to the invention may also be useful for identifying new mutations on globin genes since high levels of free α-Hb pool are indicative of the presence of mutations. Hence, if no known mutation is identified after genotyping, one skilled in the art is incited to look for such new mutations.

Definitions

As used herein, the term "α-Hb" refers to a 141 amino acid protein also called hemoglobin, alpha 1 (HBA1), alpha globin chain or alpha chain. α-Hb protein corresponds to GenBank accession number NP_000549. Usually, in healthy subjects, adult human hemoglobin (Hb A) consists of four protein subunits, two subunits called alpha hemoglobin and two subunits called beta hemoglobin.

As used herein, the terms "free α-Hb" or "free α-Hb pool" correspond to the alpha globin chains (or monomers) which are not bound to beta hemoglobin in red blood cells or reticulocytes, but could be linked to AHSP. Thus, free α-Hb corresponds to the relative excess of alpha globin chains which are not bound to the red blood cell membranes or not aggregated (inclusion bodies). In the β-thalassemia, the inclusion bodies have been shown convenient to consist only of a globin chain which have some attached heme in the form of hemichromes (Fessas et al., 1966).

As used herein, the terms "Alpha-Hemoglobin Stabilizing Protein" or "AHSP" refers to a 102 amino acid protein which is highly conserved in humans, pigs, cows, and rats. AHSP is also sometimes referred to in the art as Erythroid Differentiation Related Factor (EDRF), or Erythroid Associated Factor (ERAF). Genbank accession number for AHSP includes *Homo sapiens*, Accession Number AF485325. AHSP may also refer to a mutant AHSP with higher affinity for α-Hb than native AHSP.

As used herein, "detecting" means determining if free α-Hb is present or not in a biological sample and "quantifying" means determining the amount of free α-Hb in a biological sample.

As used herein, the term "hemoglobin-related disorder" refers to any disorder which is characterized by an imbalance in the synthesis of hemoglobin chains and notably by an excess in α-Hb.

As used herein, the term "subject" denotes a mammal, such as a rodent, a feline, a canine, and a primate. Preferably a subject according to the invention is a human.

As used herein, the term "antibody" refers to a protein capable of specifically binding an antigen, typically and preferably by binding an epitope or antigenic determinant or said antigen. The term "antibody" also includes recombinant proteins comprising the binding domains, as well as variants and fragments of antibodies. Examples of fragments of antibodies include Fv, Fab, Fab', F(ab')2, dsFv, scFv, sc(Fv) 2, diabodies and multispecific antibodies formed from antibody fragments.

The Invention

A first aspect of the invention is a method for diagnosing and/or staging a hemoglobin-related disorder in a subject in need thereof.

According to this first aspect, said method comprises the following steps of:
  contacting a biological sample obtained from said subject with an alpha hemoglobin (α-Hb)-specific binding partner selected from the group consisting of Alpha-Hemoglobin Stabilizing Protein (AHSP), beta hemoglobin (β-Hb) and an antibody that binds specifically to α-Hb,
  detecting and/or quantifying the amount of free α-Hb in said biological sample, and
  correlating said amount of free α-Hb with the diagnosis and/or the staging of a hemoglobin-related disorder in said subject.

The amount of free α-Hb quantified may thus be compared with the corresponding amount detected in the samples of control subjects, in previous samples obtained from the subject or with normal reference values.

While the method of the invention is intended for the diagnosis of a hemoglobin-related disorder, control subjects are for example subjects that have not been diagnosed for said hemoglobin-related disorder. Normal reference values refer to the amount of free α-Hb that can be determined by the method of the invention in a subject that has not been diagnosed for a hemoglobin-related disorder.

In one embodiment of the invention, said control value or reference value is determined by using the average values obtained from at least 10, preferably from at least 100 control subjects.

Quantifying the amount of free α-Hb is also of interest for monitoring for example a therapeutic treatment against said hemoglobin-related disorder such as for example a treatment with iron, cobalamin, erythropoietin or any γ chain synthesis stimulating agent.

Thus, a second aspect of the invention is a method for monitoring a treatment against said hemoglobin-related disorder in a subject in need thereof.

According to this second aspect, said method comprises the following steps of:
  contacting a biological sample obtained from said subject with an alpha hemoglobin (α-Hb)-specific binding partner selected from the group consisting of Alpha-Hemoglobin Stabilizing Protein (AHSP), beta hemoglobin (β-Hb) and an antibody that binds specifically to α-Hb,
  detecting and/or quantifying the amount of free α-Hb in said biological sample, and
  correlating said amount of free α-Hb with the monitoring of a treatment against said hemoglobin-related disorder in said subject.

According to the invention, the biological sample susceptible to contain free α-Hb is a biological sample, such as cell lysates (hemolysate or lysate of heterotopic or orthotopic hematopoietic tissues such as bone marrow, fetal liver or spleen) or is a body fluid such as serum, plasma, whole blood or cord blood.

In one embodiment, said biological sample is whole blood.

In another embodiment, said biological sample is an erythroid cells hemolysate. Example of said erythroid cells hemolysate is a reticulocyte and red blood cell hemolysate.

According to the invention, said hemoglobin-related disorder is β-thalassemia, including the Hb E related syndroms, γ-thalassemia, syndromic thalassemia conditions, acquired forms of β-thalassemia, anemia, sickle cell disease or unstable Hb variants and hereditary persistence of fetal Hb.

In one embodiment, said hemoglobin-related disorder is β-thalassemia.

In another embodiment, said hemoglobin-related disorder is a disorder leading to an imbalance in the synthesis of hemoglobin chains which is not hereditary, such as for example hyperthyroidism or some chronic viral infection.

According to the invention, said therapeutic treatment against said hemoglobin-related disorder is a treatment with iron, erythropoietin, cobalamin, or any γ chain synthesis stimulating agent.

In another embodiment, the method according to the invention is useful in order to monitoring the side effects of a treatment on the balance in the synthesis of hemoglobin chains. Examples of said treatments showing side effects include, but are not limited to, thyroid hormone, antineoplasic drugs such as hydroxyurea (hydroxycarbamide) and folates or antiviral drugs.

The method according to the invention is also useful for monitoring the clinical grade and treatment efficacy of chronic viral diseases known to modify Hb $A_2$ and Hb F expression as well as biosynthetic globin chain ratio, the magnitude of the related changes being possibly correlated to the severity of the infection but also the cellular effect of hyperthyroidism or thyroid hormone administration.

According to the invention, the α-Hb-specific binding partner susceptible to be used is selected from the group consisting of Alpha-Hemoglobin Stabilizing Protein (AHSP) and beta hemoglobin (β-Hb) and an antibody that binds specifically to α-Hb.

Antibodies useful in the various embodiments of the invention encompass commercially available antibodies and antibody fragments, as well as any novel antibodies generated to bind to a suitable epitope on α-Hb. The antibodies used in various embodiments exemplified herein are monoclonal or polyclonal in nature. Other antibodies and antibody fragments, such as recombinant antibodies, chimeric antibodies, humanised antibodies, Fab or Fv fragments are also useful.

Examples of said antibodies directed to an epitope on α-Hb include, but are not limited to, the polyclonal antibody anti-Hb α (reference P69905 of Millipore; reference ab19191 of abcam), and the monoclonal anti-Hb α antibodies obtained from a partial recombinant α-Hb (amino acid 32 to 141) with GST tag (reference WH0003039M2 of Sigma-Aldrich; reference H00003039-Q01 of Abnova).

In one embodiment, said α-Hb-specific binding partner is AHSP.

In a preferred embodiment, the AHSP is produced by genetic engineering as a fusion protein with glutathione S transferase (GST). The AHSP can be expressed with other gene fusion expression systems. Example of gene fusion expression systems include such thioredoxin, Maltose Binding Protein (MBP), Green Fluorescent Protein (GFP), Yellow Fluorescent protein (YFP), intein, NusA or luciferase as fusion proteins. The AHSP can also be expressed with the polypeptide protein Tag such as polyhistidine Tag, Strep-Tag, FLAG-Tag, S-Tag, Dsb A Tag, Dsb C tag, hemagglutinin Tag (HA-Tag) or myc-Tag.

In one embodiment of the invention, the detection and/or quantification of the free α-Hb is carried out by photometry.

In one preferred embodiment, the detection and/or quantification of the free α-Hb is carried out by spectrophotometry.

According to the invention, said α-Hb-specific binding partner may be coated directly or indirectly to a solid support, said solid support comprising a protein binding surface such as a microtiter plate, a colloid metal particle, an iron oxide particle, a latex particle or a polymeric bead or a column such as a GST microspin column (GST SpinTrap, GE Healthcare, Lifescience) or a nickel bead column or any affinity support that recognizes specifically the Tag or fusion moiety.

In one particular embodiment, the α-Hb-specific binding partner coated to a solid support is GST-AHSP. According to this embodiment, the α-Hb bound to GST-AHSP fixed on GST microspin column was eluted and the amount of retained α-Hb was measured by calculating the amount of free α-Hb in the biological sample.

In this embodiment, the method for diagnosing and/or staging a hemoglobin-related disorder or the method for monitoring a treatment against said hemoglobin-related disorder in a subject in need is achieved by:
  contacting said biological sample with GST-AHSP fixed on GST microspin column,
  eluting the α-Hb (complexed to GST-AHSP) thus retained, and
  calculating the amount of free α-Hb in the biological sample.

The amount of Hb chains are determined by absorbance, since the concentration (c) is given by c=A×1/ε where A is the observed absorbance (in od), 1 is the optical pathlength, and ε is the extinction coefficient units per M per cm. The A and ε at 415 nm are typically used, being near the peak of the Soret band.

In one embodiment, the quantity of α-Hb bound to GST-AHSP obtained after elution is calculated in mg α-Hb bound/mL hemolysate according to the equation 1:

$$\frac{A_{413} \times MM1 \times v1}{\varepsilon_{413}} \qquad \text{(equation 1)}$$

The quantity of total subunits contained in the hemolysate is calculated in mg subunits/mL hemolysate according to the equation 2:

$$\frac{A_{415} \times MM2 \times v2}{\varepsilon_{415}} \qquad \text{(equation 2)}$$

wherein $A_{413}$ and $A_{415}$ are the absorbance,
$\varepsilon_{413}$ and $\varepsilon_{415}$ are an extinction coefficient (125679 $M^{-1} \cdot cm^1$ and 125 000 $M^{-1} \cdot cm^1$, respectively),
MM1 is the molecular mass of α-Hb subunit (15744 Da)
MM2 is the molecular mass of subunits (16115 Da),
v1 is the elution volume of α-Hb bound to GST-AHSP exprimed in mL, and
v2 is the dilution factor of the hemolysate used to the assay Hb.

Thus, the amount of mg α-Hb bound to the GST microspin column per mg of subunits in one mL of hemolysate is the ratio equation 1/equation 2.

Moreover, considering both that the MM1 and MM2 are similar, and secondly that $\varepsilon_{415}$ and $\varepsilon_{413}$ are also similar, the ratio equation 1/equation 2 can be simplified. Note that the values are similar for the α-Hb-AHSP complex and the average of the Hb chains, but not identical; an exact calculation would require the specific values. If one prefers to calculate the amount by mass, rather than concentration, then the specific values of the MM (molecular mass) of the subunits of Hb are required.

It results that quantity of mg α-Hb bound/mg of subunits/mL of hemolysate is calculated according to the equation 3:

$$\frac{A_{415}^1 \times v1}{A_{415}^2 \times v2} \qquad \text{(equation 3)}$$

In a preferred embodiment, 0,500 mL of hemolysate were applied on microspin column and the α-Hb bound to GST-AHSP was recovered in 0,200 mL eluted buffer. To report the amount per mL of hemolysate, v1 is equal to 0.2×2 that is 0.4. The concentration of total subunits contained in the hemolysate was measured after a 400 fold dilution, v2 is equal to 400. The ratio v1/v2 is equal to 1/1000.

Therefore, after simplification of the equation 3, the quantity of μg α-Hb bound/mg of subunits/mL of hemolysate is calculated according to the equation 4:

$$\frac{A_{415}^1}{A_{415}^2} \qquad \text{(equation 4)}$$

Thus, a simple report of absorbance is sufficient in our experiment to obtain the quantity in μg of free α-Hb according to the quantity of total α- and β-Hb (on heme basis) contained in one mL of hemolysate. The obtained amount of free α-Hb detected with assay is ranged from 0.010 μg/mg to 0.85 μg/mg. To facilitate the comparison of different obtained quantities, the α-Hb free is given in ng/mg ie ppm.

In another embodiment, the fraction of free α-Hb chains relative to the total number of all Hb chains (f) is calculated according to the following Formula 1:

$$(f)=[A(\alpha\text{-}Hb)/A(Hb \text{ total})]*s*d \qquad \text{(Formula 1)}$$

wherein A is the absorbance and s and d are a correction factors to take into account any differences in dilution (d) or absorption coefficients (s). For typical experiment, the dilution factor d and s is approximately 1.

The units of ppm (f*1 000 000) or % (f×100) are appropriate in this case:
- a ppm value inferior to 150 is indicative of said patient is not affected by a hemoglobin-related disorder, except to the α-thalassemia;
- a ppm value comprised between 150 and 400/450 ppm is indicative of said patient is affected by moderate hemoglobin-related disorder in which there is a relative defect a to β globin chain synthesis; and
- a ppm value superior to 450 is indicative of said patient is affected by a clinically significant β-thalassemia, a severe hemoglobin-related disorder.

As used herein, the term "ppm" corresponds to the fraction of free α-Hb relative to total Hb subunits. Thus, a value corresponding to 80 ppm corresponds to 0.008% of free α-Hb relative to total Hb subunits, equivalent to a captured amount of 80 ng free α-Hb per mg of total Hb.

In another embodiment, the detection and/or quantification of the free α-Hb is carried out by immunological detection.

In one embodiment, the immunological detection or quantification of the free α-Hb pool is achieved by any methods known in the art using at least one antibody that binds specifically to α-Hb.

Examples of said methods include, but are not limited to, standard electrophoretic and immunodiagnostic techniques such as western blots, immuno-precipitation assay, radioimmunoassay, ELISA (enzyme-linked immunosorbent assay), "sandwich" immunoassay, gel diffusion precipitation reaction, immunodiffusion assay, precipitation reaction, agglutination assay (such as gel agglutination assay, hemagglutination assay, etc.), complement fixation assay, protein A assay, immunoelectrophoresis assay, high performance liquid chromatography, size exclusion chromatography, solid-phase affinity, etc.

According to the invention, an antibody that binds specifically to α-Hb is an antibody that does not cross react with other hemoglobins such as β-Hb.

Examples of said antibody include, but are not limited to, the polyclonal antibody anti-Hb α (reference P69905 of Millipore; reference ab19191 of abcam), and the monoclonal anti-Hb α antibodies obtained from a partial recombinant α-Hb (amino acid 32 to 141) with GST tag (WH0003039M2 of Sigma-Aldrich; H00003039-Q01 of Abnova).

According to the invention, the antibody that specifically binds to α-Hb may be labelled with a detectable molecule or substance. Examples of suitable labels for this purpose include a chemiluminescent agent, a colorimetric agent, an energy transfer agent, an enzyme, a substrate of an enzymatic reaction, a fluorescent agent. The label may be coupled directly or indirectly by any known method in the art.

In another embodiment of the invention, the quantification of free α-Hb in a biological sample may be achieved by the flash photolysis technique. The α-Hb, trapped by AHSP or another molecule, can be subjected to photodissociation. The time resolved change in absorption can provide both the quantity and information on the type of hemoprotein that was trapped. For example, one could distinguish the chain type or a contamination by free heme.

In one embodiment, the detection or quantification of free α-Hb in a sample may be achieved by a protein chip array system, wherein the antibody that specifically binds to α-Hb is coated directly or indirectly on a protein chip array. The sample to be tested is labelled by biotinylation in vitro. Biotinylated free α-Hb trapped on the array are then detected by avidin or streptavidin which strongly binds biotin. If avidin is conjugated with horseradish peroxidase or alkaline phosphatase, the captured free α-Hb can be visualized by enhanced chemical luminescence. The amount of protein bound to the antibody that specifically binds to α-Hb represents the level of free α-Hb in the sample. Other methods, like immunochemical staining, surface plasmon resonance, matrix-assisted laser desorption/ionization-time of flight, can also be used to detect the captured proteins.

In another embodiment of the invention, the detection or quantification of free α-Hb in a sample may be achieved by a cytometric bead array system wherein the antibody that specifically binds to α-Hb is coated directly or indirectly on beads.

In another embodiment of the invention, the detection or quantification of free α-Hb in a biological sample may be achieved by a competitive immunoassay.

Examples of competitive immunoassays include enzyme immunoassay or enzyme-linked immunoassay (EIA or ELISA), fluorescent immunoassay, magnetic separation assay (MSA), lateral flow assay, diffusion immunoassay or immunoprecipitation immunoassay.

In one example of competitive immunoassay, the quantification of free α-Hb is achieved by
  combining a sample containing free α-Hb with a known amount of a labelled α-Hb to create a spiked sample,
  binding labelled and unlabelled free α-Hb in the spiked sample with an antibody anti-α-Hb, wherein the antibody binds specifically to α-Hb to create complexes and to labelled α-Hb to create labelled complexes,
  measuring the amount of labelled complex
  calculating the amount of free α-Hb present in the sample.

In one embodiment, said antibody that specifically binds to α-Hb may be coated to a solid support, said solid support comprising a protein binding surface such as a microtiter plate, a colloid metal particle, an iron oxide particle, a latex particle or a polymeric bead.

In one embodiment, the labelled α-Hb may comprise a label such as a chemiluminescent agent, a colorimetric agent, an energy transfer agent, an enzyme or a fluorescent agent. Examples of chemiluminescent agent include an enzyme that produces a chemiluminescent signal in the presence of a substrate(s) that produces chemiluminescent energy when reacted with the enzyme. Examples of such an enzyme include horseradish peroxidase (HRP) and alkaline phosphatase (AP). Other examples of a chemiluminescent agent include a non-enzymatic direct chemiluminescent label, such as Acrinidium ester system. Examples of a colorimetric agent include an enzyme such as horseradish peroxidase, alkaline phosphatase, and acetylcholine esterase (AChE). Examples of energy transfer agent include fluorescent lanthanide chelates. Examples of fluorescent agents include fluorescent dyes.

While the spiked sample is incubated with the antibody that binds to α-Hb, the free α-Hb present in the sample and the added labelled α-Hb compete for binding to the antibody. Labelled α-Hb will then be able to bind the antibody depending on the relative concentration of the unlabeled free α-Hb present in the sample. Thus, when the amount of labelled α-Hb is measured, it is inversely proportional to the amount of unlabeled free α-Hb present in the sample. The amount of free α-Hb present in the sample may then be calculated based on the amount of labelled α-Hb measured, using standard techniques.

In another example of competitive immunoassay, the quantification of free α-Hb is achieved by the antibody coupled with or conjugated with a ligand, said ligand binding to an additional antibody added to the sample. One example of said ligand is fluorescein. The additional antibody may be bound to a solid support. In this example of competitive immunoassay, the additional antibody binds to the ligand coupled with the antibody that binds in turn to (i) free α-Hb present in the sample and (ii) labelled α-Hb added to the sample. Said mass complex formed allows isolation and measurement of the signal generated by the label coupled with the labelled α-Hb.

In another example of competitive immunoassay, α-Hb may be bound to a solid support, and incubated with (i) an antibody that binds to α-Hb and (ii) a sample containing the free α-Hb to be measured. The antibody binds either the α-Hb bound to the solid support or the free α-Hb present in the sample, in relative proportion depending of the concentration of the free α-Hb present in the sample. The antibody that binds to α-Hb bound to the solid support is then bound to another antibody that is coupled with a label. The amount of signal generated from the label is then detected to measure the amount of α-Hb. Such a measurement will be inversely proportional to the amount of free α-Hb present in the sample. Such an assay may be used in a microtiter plate.

In another example of competitive immunoassay, the free α-Hb to be measured compete with α-Hb that is bound to a first solid support particle, such as Ficoll, for the antibody that is bound to or coated to a second solid support particle. Cross-binding or agglutination between the particles occurs and forms clumps of co-agglutination lattice. The amount of agglutination may be measured using standard techniques, such as spectrophotometry.

In another embodiment of the invention, the quantification of free α-Hb in a biological sample may be achieved by a non-competitive immunoassay referred as immunometric, "two-site" or "sandwich" immunoassays, wherein free α-Hb may be bound to or sandwiched between two antibodies that specifically bind to α-Hb.

Examples of non-competitive immunoassays include enzyme immunoassay or enzyme-linked immunoassay (EIA or ELISA), fluorescent immunoassay, magnetic separation assay (MSA), lateral flow assay, diffusion immunoassay, immunoprecipitation immunoassay, immunosorbent or "antigen-down" assay using antibodies that bind to α-Hb bound to a solid support, or agglutination assay.

In this embodiment, the quantification of free α-Hb in a biological sample is achieved by
  contacting said sample with two antibodies that bind to α-Hb,
  measuring the amount of bound anti-α-Hb antibody and calculating the amount of free α-Hb in the biological sample.

In one embodiment of the invention, the first antibody that binds to α-Hb is an antibody directed to an epitope in a first domain of α-Hb and the second antibody is an antibody directed to another epitope in a second domain of α-Hb.

In one embodiment, a one-step assay (simultaneous incubation of the two antibodies that bind to α-Hb) is useful. In another embodiment, a two-step assay (sequential incubation of the two antibodies that bind to α-Hb) is useful. A two-step assay is preferred in the case where other molecules could compete for binding to the antibodies that bind to α-Hb.

In one embodiment, one antibody that binds to α-Hb is the "capture" antibody, and is bound to a solid support, such as protein coupling or protein binding surface, colloid metal particles, iron oxide particles, or polymeric beads. One example of polymeric beads is a latex particle. In such an embodiment, the capture antibody is bound to or coated on a solid phase support using standard non-covalent or covalent binding methods, depending on the required analytical and/or solid phase separation requirements. The solid support may be in the form of test-tubes, beads, microparticles, filter paper, membrane, glass filters, magnetic particles, glass or silicon chips or other materials known in the art. The use of microparticles, particularly magnetisable particles, that have been directly coated with the antibody or particles that have been labelled with a universal binder (such as avidin or anti-species antibody) is useful for significantly shortening the assay incubation time.

Alternatively, the capture anti-α-Hb antibody may be coupled with a ligand that is recognized by an additional antibody that is bound to or coated on the solid support. Binding of the capture antibody to the additional antibody via the ligand then indirectly immobilizes the capture antibody on the support. An example of such a ligand is fluorescein. Alternatively, the binding partner may also be detected indirectly by a secondary detection system. Said secondary detection system is based on several different principles known in the art such as antibody recognition and other forms of immunological or non-immunological bridging and signal amplification detection systems (for example, the biotin-streptavidin system). When a signal amplification system is used, the label includes a first protein such as biotin coupled with the capture antibody, and a second protein such as streptavidin that is coupled with an enzyme. The second protein binds to the first protein. The enzyme produces a detectable signal when provided with substrate (s), so that the amount of signal measured corresponds to the amount of binding partner that is bound α-Hb. Examples of enzymes include, without limitation, alkaline phosphatase, amylase, luciferase, catalase, beta-galactosidase, glucose oxidase, glucose-6-phosphate dehydrogenase, hexokinase, horseradish peroxidase, lactamase, urease and malate dehydrogenase. Suitable substrates include, without limitation, TMB (3,3',5,5'-tetramethyl benzidine), OPD (o-phenylene diamine), and ABTS (2,2'-azino-bis (3-ethylbenzthiozoline-6-sulfonic acid). The signal amplification approach may be used to significantly increase the assay sensitivity and low level reproducibility and performance.

Antibodies useful in the various embodiments of the invention encompass commercially available antibodies and antibody fragments, as well as any novel antibodies generated to bind to a suitable epitope on α-Hb. The antibodies used in various embodiments exemplified herein are monoclonal or polyclonal in nature. Other antibodies and antibody fragments, such as recombinant antibodies, chimeric antibodies, humanised antibodies, Fab or Fv fragments are also useful.

In another embodiment, the quantification of free α-Hb in a biological sample may be achieved by homogeneous time resolved fluorescence (HTRF).

For example, a first antibody directed to an epitope in a first domain of α-Hb is coupled with a donor fluorophore, such as Europium cryptate (Eu3+ cryptate) or Lumi4™-Tb (Tb2+ cryptate), and a second antibody directed to a second domain of α-Hb is coupled with an acceptor such as XL665, a modified allophycocyanin.

Another aspect of the invention is a kit for use in the method of the invention as described here above, said kit comprising, as separate elements:
a solid support, and
an α-Hb-specific binding partner.

In one embodiment, said α-Hb-specific binding partner is AHSP.

In a preferred embodiment, ASHP is fused to GST.

In another embodiment, said α-Hb-specific binding partner is coated directly or indirectly to a solid support, said solid support comprising a protein binding surface such as a microtiter plate, a colloid metal particle, an iron oxide particle, a latex particle or a polymeric bead or a column such as a GST microspin column or a nickel bead column or any affinity support that recognizes specifically the Tag or fusion moiety.

In one preferred embodiment, said solid support is a GST microspin column.

In a particular preferred embodiment, GST-AHSP is fixed on GST microspin column.

The kit may also contain optional additional components for performing the method of the invention. Such optional components are for example containers, mixers, buffers, instructions for assay performance, labels, supports, and reagents necessary to elution.

The following examples are given for the purpose of illustrating various embodiments of the invention.

After expression and purification, 400 μg of GST-AHSP was bound to the microspin column containing 50 μL of Glutathione Sepharose 4B and was then incubated with hemolysates of patients to capture the free α-Hb. After a 30 minute incubation at 4° C. under gentle agitation, the microspin column was washed five times with PBS (150 mM NaCl, 10 mM $Na_2HPO_4$, pH 7.4) and the bound proteins were eluted by 200 μL glutathione buffer (10 mM reduced glutathione in 50 mM Tris-HCl buffer at pH 8.0). The α-Hb containing in the elution fraction was quantified by spectrophotometry at 414 nm ($\epsilon = 125$ $mM^{-1} \cdot cm^{-1}$) with a HP 8453 spectrophotometer. The total quantity of subunits of Hb in 1 mL of hemolysate was also determined at 414 nm after a 400 fold dilution. The fraction of free α-subunits is thus simply the ratio of absorption of eluted α-subunits from the column on the absorption of total subunits of Hb and is reported in ng/mg equivalent to ppm.

In vitro assays were made for some patients from different blood samples and the measured values of free α-Hb pool are consistently similar.

Figure 2:
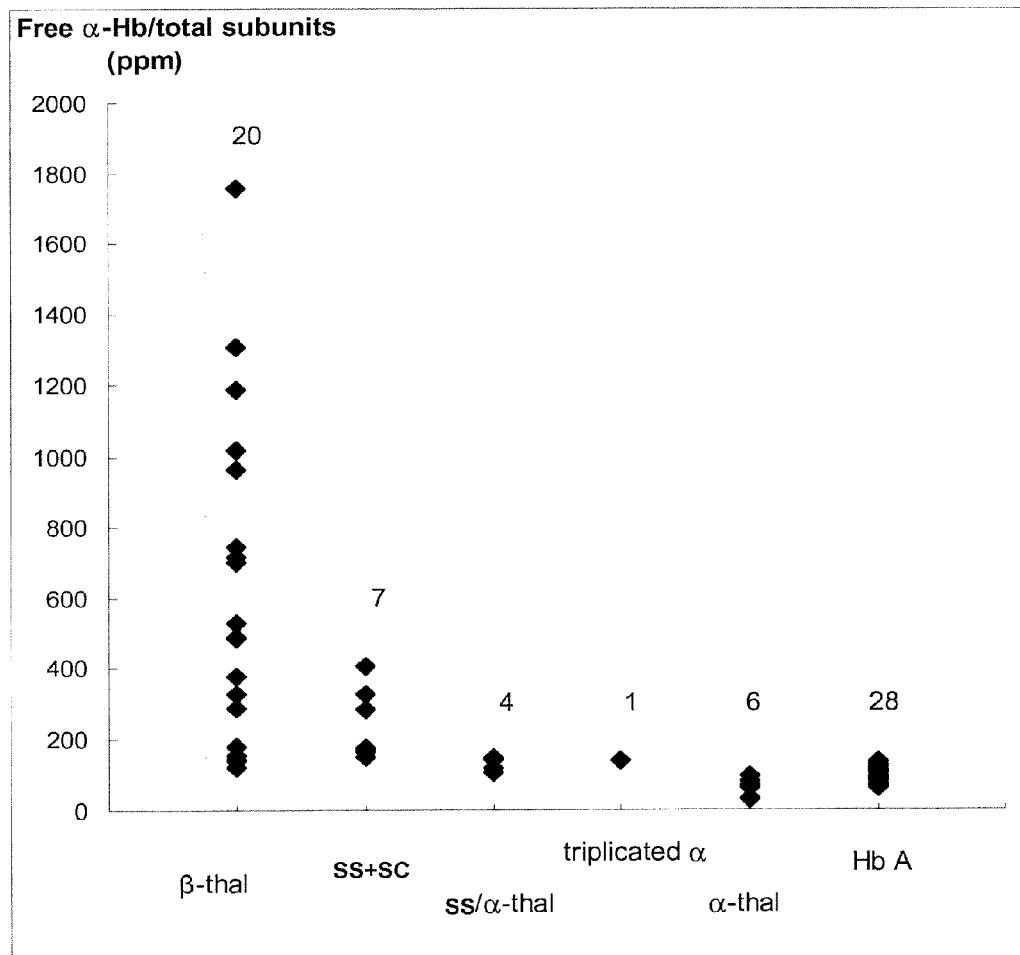

FIG. 2: Free α-Hb dosing assay applied to β-thalassemic patients compared to patients exhibiting different pathologies of hemoglobin and to patients without Hb abnormality (HbA):

This study concerns 66 patients (43 males and 23 females; mean age, 50±17 years) including 20 β-thalassemic patients (12 males and 8 females; mean age, 39±15 years), 7 SS or SC patients (4 males and 3 females; mean age, 36±9 years), 4 patients SS/α-thal (3 males and 1 female, mean age, 39±8 years) and 1 male triplicated α patient (69 years), 6 α-thalassemic patients (2 males and 5 females; mean age, 47±15 years) and 28 patients with Hb A (reference group: 21 males and 7 females; mean age, 63±11 years). The observed fraction of free α-Hb relative to total Hb (both subunits) is expressed as ppm, equivalent to ng of free α-Hb per mg total (α+β) subunits.

Figure 3:
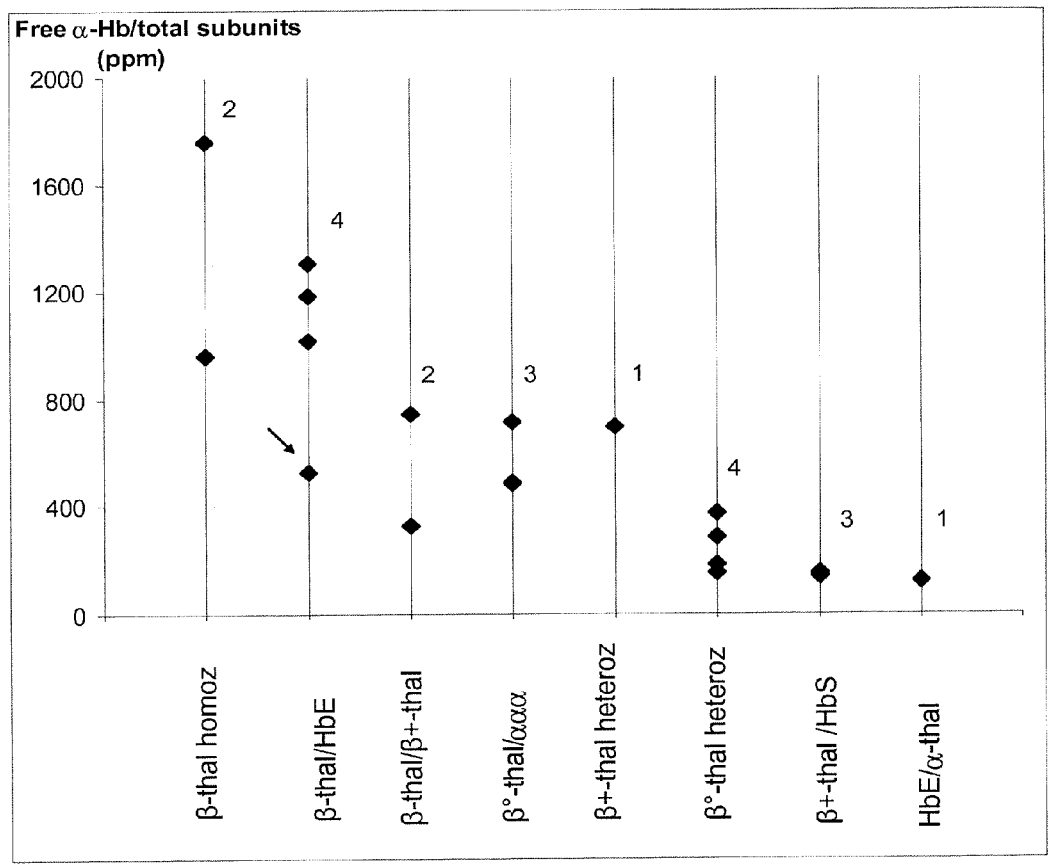

FIG. 3: Free α-Hb dosing assay applied to 20 β-thalassemic patients grouped by their globin genotype:

The number of patients studied is indicated above each genotype. For the 2 patients with homozygous β-thal, one patient is $β^+$-thal and the other is $β^0$-thal. In the 4 patients with β-thal/HbE, 1 patient is $β^+$-thal and three are $β^0$-thal. The 3 patients with $β^0$-thal heterozygous associated to a triplication of α-gene belong to the same family.

The arrow indicates the patient number 5 in the Table 1B.

Figure 4:
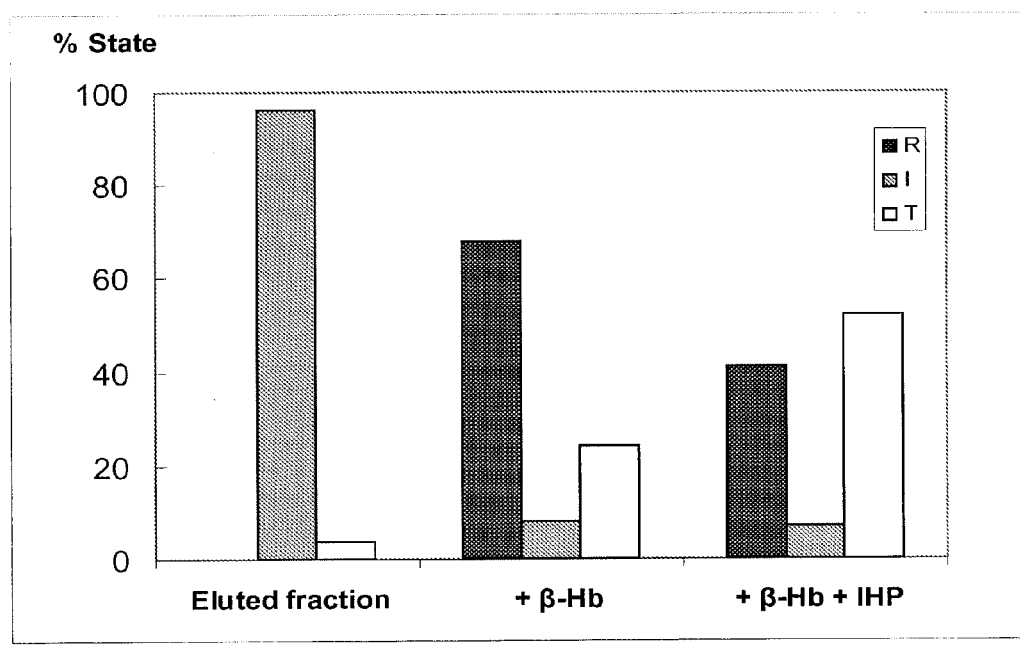

FIG. 4: Characterization of the α-subunits in the eluted fraction by CO recombination kinetics after photo-dissociation:

The bimolecular recombination kinetics were measured after flash-photolysis using 10 ns YAG laser pulses (Quantel, Les Ulis, France) at 532 nm. Samples were in 4×10 mm quartz cuvettes with observation at 436 nm. Measurements were at 25° C. in glutathione buffer, 100 μM CO. In a second measurement, β-Hb was added. Then, Inositol Hexaphosphate (IHP), an analogue of the 2,3-DiPhosphoGlycerate effector, was added at a final concentration of 1 mM to enhance the fraction of T state tetrameric Hb.

Figure 5:
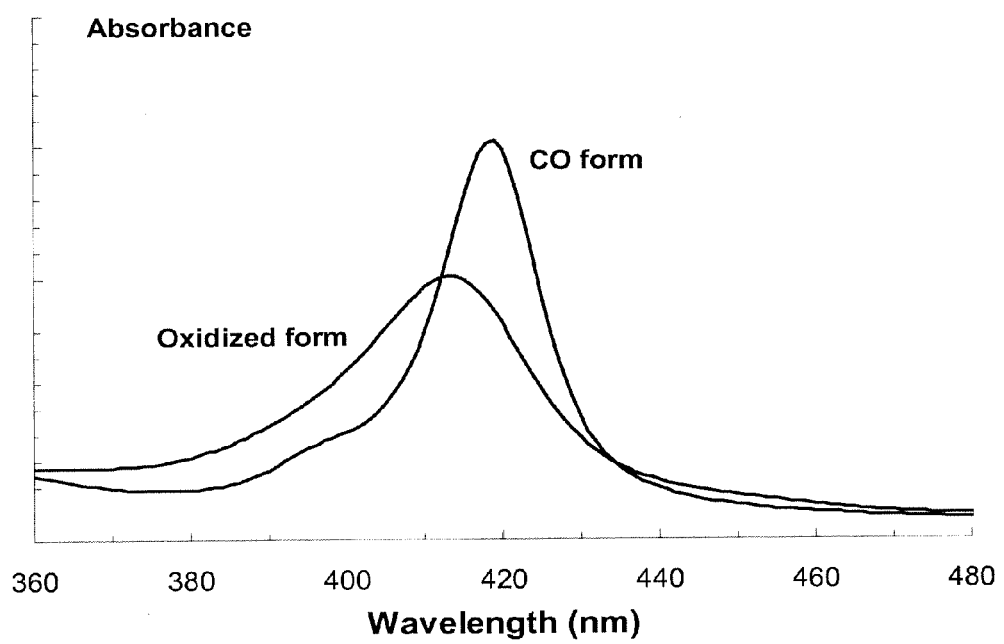

FIG. 5: Characterization of the α-subunits in the eluted fraction by spectrophotometry:

Two cases are shown here: the absorption spectra of ferrous α-Hb in the CO form and the α-Hb/AHSP complex in the oxidized (His-Fe-His hexacoordinated) form.

EXAMPLE

Material & Methods

Patients:

This study concerns 66 patients (43 males and 23 females) including 28 patients without apparent Hb disorder (reference group) (21 males and 7 females; mean age, 63±11 years), 20 β-thalassemic patients (12 males and 8 females; mean age, 39±15 years), 6 α-thalassemic patients (2 males and 4 females; mean age, 50±15 years), 7 SS or SC patients (4 males and 3 females; mean age, 36±9 years), 4 patients SS/α-thal (3 males and 1 female, mean age, 39±8 years) and 1 male triplicated α patient (69 years) For patients, except the controls without apparent Hb disorder, the β- and α-thal genotypes were determined. An informed consent was obtained from all participants to this study according to the international Helsinki declaration and French ethical regulations.

Hematological and Genotyping Investigations:

EDTA-anticoagulated Venous Blood samples was collected during routine sampling for the current follow-up of their clinical conditions. Hb phenotype was investigated by cation-exchange chromatography (BioRad Variant II hemoglobin Analyzer®). Patients with no apparent Hb were sampled at the time of a scheduled phlebotomy for iron overload treatment. All of them had their blood cell count and serum ferritin determination. Patients with ongoing infectious or inflammatory diseases, dysthyroïdism or chronic viral diseases were not included.

In all β- and α-thalassemic patients, the DNA extracted from peripheral blood and the genotyping of the β-globin locus and α-globin locus was done using conventional methods (Rose et al. 2009)

Preparation of the Red Blood Cell Hemolysate, the GST-AHSP Protein and the α-Hb:

Red blood cells (RBC) were prepared within 2 hours following blood collection. RBC were washed with 0.15 M NaCl and lysed by cold water. After centrifugation, the red cell lysate was recovered and kept at −80° C.

Recombinant AHSP was expressed as fusion protein with glutathione-S-transferase (GST) in *Escherichia coli* using the pGEX-AHSP expression plasmid and purified as previously described (Baudin-Creuza et al. 2004)

Native α-Hb was purified from Hb A as previously described (Geraci et al. 1969 and Parkhurst et al. 1992)

In Vitro Free α-Hb Dosing Assay:

Five hundred μL of hemolysate or 500 μg of native α-Hb (control) were applied on a GST Spin Trap™ column (Glutathione Sepharose 4B, GE Healthcare, Life Science) on which 400 μg GST-AHSP were bound. After incubation and washing, the GST-AHSP and the bound proteins were eluted. The α-Hb bound to GST-AHSP and the total quantity of Hb ($α_2β_2$) contained in hemolysate were quantified by spectrophotometry at 414 nm. The fraction of free α-Hb is thus simply the ratio of absorption of eluted α-Hb from the column on the absorption of total Hb and is reported in ng/mg or ppm. To confirm that the eluted proteins on column are α-Hb, we followed at 436 nm the CO rebinding kinetics after flash photolysis.

Competitive In Vitro Study:

To determine if α-Hb associated with AHSP in the hemolysate could interfere with our assay, we achieved a competitive in vitro study. After binding of GST-AHSP on the micro-column, free AHSP/α-Hb complex was added at equimolarity in AHSP. The flow-through fraction was recovered, then the column was washed, and the remained bound proteins were eluted. The α-Hb contained in the different fractions was determined at 414 nm.

Results

Figure 1:
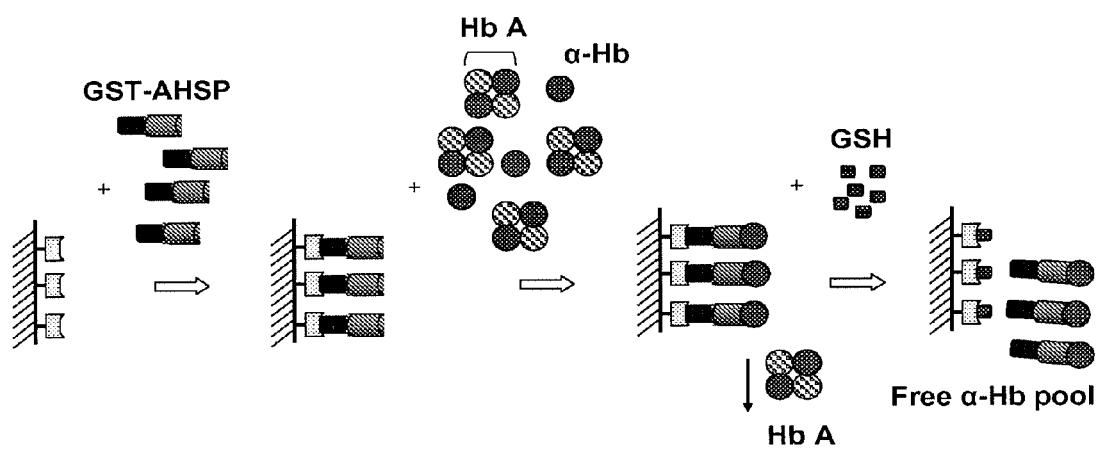
FIG. 1: Principle of the free α-Hb dosing assay.

In β-thalassemic patients, the defective β-globin leads to an imbalance in the synthesis of the α- and non α-globin chains. Many studies of Hb synthesis clearly showed that β-chain synthesis is significantly less than α-chain synthesis. Since the problem is excess α chain, it is appropriate to quantify accurately the amount of free α-Hb, but to date, there was no more method to evaluate this parameter. In this study, we describe a new method to measure the amount of free α-Hb containing in the hemolysate of β-thalassemic patients using the chaperone AHSP to trap free α-chains (FIG. 1).

Identification of the Proteins Bound to GST-AHSP from Hemolysate of Patients:

To confirm that the protein bound to GST-AHSP is α-Hb, we measured the CO rebinding kinetics after flash photolysis, since the AHSP/α-Hb complex displays a unique rate "I", which is intermediate to the usual R and T-states of Hb (Baudin-Creuza et al., 2004). The CO recombination kinetics of the eluted complex exhibit a single intermediate phase with the same "I" rate as reported for α-Hb in the presence of its chaperone (FIG. 4). After addition of β-Hb to the eluted complex, the recombination kinetics became biphasic, with rates characteristic of the allosteric R and T states of tetrameric Hb. As expected for normal tetrameric Hb, IHP enhances the amount of slow (T state) phase. The ligand binding characteristics of the eluted fraction demonstrate that functional α-Hb was trapped with AHSP and can be transferred to β-Hb to form Hb A with the correct allosteric behavior (FIG. 4). We then quantified the eluted proteins bound to GST-AHSP by spectrophotometry at 414 nm (FIG. 5). The observed spectra of the elution fraction is identical to that obtained for α-Hb in the presence of AHSP (with or without GST), in our case the GST-AHSP/α-Hb complex.

Definition of Terms "Free α-Hb":

It has been reported that the concentration of AHSP in human RBC precursors was around 0.1 mM (Kihm et al. 2002). The question thus arises whether AHSP/α-Hb complex may still be present in the hemolysate and, if so, whether it could interfere with our assay by releasing α-Hb during its passage through the column. To answer this question, we conducted a competitive in vitro study showing that 20% of α-Hb within the AHSP/α-Hb complex were transferred to the AHSP bound to the column. These results show that the AHSP bound to the column can trap both free α-Hb and a fraction of α-Hb within the AHSP/α-Hb complex in the hemolysate. Thus, the terms "free α-Hb" or "free α-Hb pool" correspond to the α-Hb which are not bound to β-Hb in red blood cells, but could be linked to AHSP.

Quantification of Free α-Hb Pool from the Hemolysates of Patients:

As determined from 10 separate experiments, the maximal quantity of native α-Hb binding to GST-AHSP attached to microspin column was 99±11 μg.

The free α-Hb dosing assay was applied to the hemolysates of 66 subjects. The amount of free α-Hb captured relative to total amount of Hb (both subunits) applied to the column varies between 29 and 1756 ppm (ng of free α-Hb per mg total Hb) (FIG. 2).

In the hemolysate of the 28 patients without Hb abnormality, which may be considered as a reference group, we found an average value of about 93±21 ppm of free α-Hb, with the lowest limit value at 62 ppm and the highest at 134 ppm. These results agree with those showing the presence of free newly synthesized α-chains in normal human reticulocytes.

In the case of the 20 β-thalassemic patients, the fraction of free α-Hb relative to total subunits varied between 119 and 1756 ppm. The high dispersion of the level of free α-Hb pool reflects the clinical spectrum of this pathology ranging from asymptomatic forms to severe diseases. In our series, when the α-Hb pool was below 140 ppm, the patient did not exhibit a symptomatic β-thalassemia. The great variability in the phenotypic expression of the β-thal often depends on the association of the β-globin defect with another hemoglobin abnormality or of another modulating factor. In Table 1-A, the β-thalassemic patients were classified in terms of α- and β-genotypes and hematological values and in FIG. 3 the free α-Hb pool is represented in relation to these genotypes.

The highest pool of free α-Hb, 1756 ppm, corresponding to 20 μg without taking into account of total subunit Hb in the hemolysate, was observed for a homozygous β$^+$-thal patient with a thalassemia intermedia phenotype. Since about 100 μg of α-Hb could bind to the column, the maximum value that could be detected is far above the values reached in pathology. In three of the four patients with β-thal/HbE, the fraction of free α-Hb was higher than 1000 ppm. In contrast, the lower value found for the fourth patient (525 ppm; patient number 5 in Table 1) was explained by the simultaneous presence of an α-thal ($\alpha\alpha/\alpha\alpha^{-3.7}$). Intermediate values were noted in the group made by β$^+$-thal heterozygous patients, compound heterozygous patients and the β$^0$-thal heterozygous patient associated to an α-gene triplication. Intermediate low values were observed for patients belonging to β$^+$-thal/Hb S or heterozygous β$^0$-thal group. The lowest value (119 ppm) was found for a heterozygous patient for Hb E associated with an α-thal ($\alpha\alpha/\alpha\alpha^{-3.7}$).

In the case of the 6 patients with α-thal (Table 1-B), the observed amount of free α-Hb was below that of the reference group, typically between 29 and 94 ppm with an average of 61 ppm±26 ppm. From our results it appears clearly that presence of the α-thal reduce significantly the value of the free α-Hb pool.

For the 7 SS or SC patients, the amounts of free α-Hb are more heterogeneous, between 161 and 403 ppm with an average of 237±99.8 ppm (FIG. 2).

For the 4 patients SS/α-thal, the amounts of free α-Hb is intermediate between that obtained with the SS or SC patients and the α-thalassemic patients, with an average of 126 ppm±18.6 ppm.

The precision of our test was exemplified by two patients who were initially considered without apparent Hb disorder and for which the free α-Hb values were found lower (33 ppm) and higher (138 ppm) than the values in the reference group. Genotyping of these patients showed that the first carried an α-thal ($\alpha^{ivs1-5nt} \alpha/\alpha\alpha$, patient 5 Table 1B), while the second patient had an α-gene triplication. These two patients were removed from the control group.

In conclusion, we report a sensitive and simple method to detect the free α-Hb pool in patients with a β-thalassemia. The free α-Hb pool not only correlated well with the clinical classification of the studied β-thalassemia, but may provide a more precise scale of severity within a given genotype. This assay may thus serve in order to refine the diagnosis for heterozygous aggravated forms and to give a biological criterion for the better classification of intermediate β-thalassemias. Furthermore the free α-Hb index clearly separates the various types of hemoglobinopathies. This assay will also allow monitoring of the evolution of the imbalance of Hb synthesis in response to treatments, such as with recombinant erythropoietin, in order to make fine adjustments of the therapy. More generally, this assay will also be applied to all diseases with an imbalance of globin synthesis.

TABLE 1

Clinical and biological features of patients of (A) β-thalassemic patients and (B) α-thalassemic patients Table 1A

| Patient | Age | Gender | Category | β genotype | α genotype | Reticulocytes x10³/mm (%) | Hb, g/dL | MC, fL* | MCH, pg** | Hb A % | Hb A$_2$ % | Other Hbs % | Free α-Hb ppm |
|---|---|---|---|---|---|---|---|---|---|---|---|---|---|
| 1 | 38 | F | β$^+$-thal homoz | IVSI-6(T > C)/IVSI-6(T > C) | αα/αα | 224 (6.1) | 8.3 | 78.4 | 22.4 | 68.3 | 4.6 | F: 13.1 | 1756 |

TABLE 1-continued

Clinical and biological features of patients of (A) β-thalassemic patients and (B) α-thalassemic patients
Table 1A

| Patient | Age | Gender | Category | β genotype | α genotype | Reticulocytes x10³/mm³ (%) | Hb, g/dL | MC, fL* | MCH, pg** | Hb A % | Hb A₂ % | Other Hbs % | Free α-Hb ppm |
|---|---|---|---|---|---|---|---|---|---|---|---|---|---|
| 2 | 35 | M | β°-thal/β°-thal | cd39(C > T)/IVS-II-1(G > A) | αα/αα | 156 (5.3) | 7.7 | 96.2 | 29.6 | 0 | 1.5 | F: 98 | 962 |
| 3 | 29 | F | β°-thal/β^E | IVSII-654(C > T)/cd26(G > A) | αα/αα | 243 (6) | 7.8 | 81.3 | 24.1 24.4 | 0 | na*** | F: 57 E + A2: 43.7 | 1304 |
| 4 | 21 | M | β°-thal/β^E | cd22(G > T)/cd26(G > A) | αα/αα | 526 (13.5) | 7.5 | 71.8 | 19.2 | 0 | na | F: 28 E + A2: 72 | 1184 |
| 5# | 54 | F | β°-thal/β^E | cd17(A > T)/cd26(G > A) | α^{-3.7}/αα | 150 (3.1) | 8.8 | 58.3 | 18.0 | 0 | na | F: 20 E: 80 | 525 |
| 6# | 52 | M | β⁺-thal/β^E | cd26(G > A)/-28(A > G) | αα/αα | 147 (7.4) | 8.1 | 63.4 | 19.8 | 21 | na | F: 9.3 E + A2: 69.7 | 1018 |
| 7 | 42 | M | severe β⁺/severe β⁺ | IVSI-5(G > A)/IVS-I 110(G > A) | αα/αα | 164 (4.6) | 10.6 | 97.2 | 29.4 | 6 | 1.5 | F: 92.5 | 742 |
| 8# | 28 | F | β°/mild β⁺-thal | IVSI-1(G > A)/-101(C > T) | αα/αα | 165 (3.6) | 9.2 | 63.0 | 20.0 | 82.5 | 6.5 | F: 11 | 325 |
| 9# | 37 | M | β°-thal/triplicated α | IVSI-1(G > A)/β^A | αα/ααα | 145 (3.1) | 9.9 | 66.0 | 21.1 | 92.2 | 5.3 | F: 2.5 | 714 |
| 10# | 36 | F | β°-thal/triplicated α | IVSI-1(G > A)/β^A | αα/ααα | 206 (3.75) | 11.2 | 63.6 | 20.4 | 90.9 | 5.1 | F: 4 | 487 |
| 11# | 62 | M | β°-thal/triplicated α | IVSI-1(G > A)/β^A | αα/ααα | 134 (2.6) | 10.9 | 66.0 | 20.6 | 88.8 | 5.2 | F: 6 | 485 |
| 12# | 55 | M | β⁺-thal heteroz | IVSII-654(C > T)/β^A | αα/αα | 112 (2.9) | 8.1 | 66.7 | 20.8 | 88.4 | 5.2 | F: 6.4 | 698 |
| 13# | 24 | M | β°-thal heteroz | cd6(-A)/β^A | αα/αα | 113 (3) | 8.2 | 67.6 | 22.2 | 87.4 | 6.1 | F: 6.5 | 284 |
| 14# | 47 | M | β°-thal heteroz | cd39(C > T)/β^A | αα/αα | 130 (2) | 12.3 | 62.5 | 19.2 | 93.3 | 5.4 | F: 1.3 | 373 |
| 15# | 52 | F | β°-thal heteroz | IVSI-1(G > A)/β^A | αα/αα | 120 (2.3) | 11.0 | 64.2 | 20.8 | 92.4 | 5.2 | F: 2.4 | 150 |
| 16# | 31 | M | β°-thal heteroz | IVSII-1(G > A)/β^S | αα/α^{-3.7} | 212 (4.2) | 11.0 | 68.6 | 21.6 | 0 | 4.1 | F: 10.7 S: 85.3 | 178 |
| 17# | 32 | M | β⁺-thal/β^S | δβ-Lepore/β^S | αα/αα | 107 (1.73) | 14.5 | 71.2 | 23.9 | 1.8 | na | F: 18.4 Lepore: 10.3 S: 69.5 | 138 |
| 18 | 24 | F | β⁺-thal/β^S | -29(A > G)/β^S | αα/αα | 132 (2.7) | 12.0 | 73.5 | 24.5 | 26 | 5 | F: 5 S: 69 | 151 |
| 19# | 31 | F | β⁺-thal/β^S | -29(A > G)/β^S | αα/αα | 152 (3.2) | 11.4 | 74.5 | 24.3 | 24.5 | 6 | F: 6.5 S: 69 | 141 |
| 20 | 81 | M | β^E/β^A | cd26(G > A)/β^A | αα/αα^{-3.7} | 21 (0.45) | 12.1 | 78.7 | 25.7 | 71 | na | F: 0.5 E + A2: 28.5 | 119 |

TABLE 1B

| Patient | Age | Gender | β genotype | α genotype | Reticulocytes x10³/mm³ (%) | Hb g/dL | MCV fL* | MCH pg** | Hb A₂ % | Other Hbs % | Free α-Hb ppm |
|---|---|---|---|---|---|---|---|---|---|---|---|
| 1 | 57 | F | β^A | -α^{-3.7}/--^{SEA} | 195 (3.75) | 9.1 | 59.6 | 17.5 | 0.6 | F: 0.8 H: 18 | 29 |
| 2 | 41 | F | β^A | α-/--^{SEA} | 185 (3.94) | 9.3 | 63.8 | 19.8 | 0.8 | F: 2 H: 18 | 70 |
| 3 | 70 | F | β^A | αα/--^{SEA} | 118 (1.93) | 13 | 68.9 | 21.3 | 1.9 | F: 0.8 | 94 |
| 4^Δ | 28 | F | β^A | αα/-- | 90 (1.67) | 10.7 | 63 | 19.8 | 2.5 | F: 0.7 | 78 |
| 5 | 58 | M | β^A | αα/αα^{ivs1 -5nt} | 81 (1.21) | 13.2 | 65.7 | 19.7 | 2 | F: 0.3 | 33 |
| 6 | 44 | M | β^A/cd26(G > A) | αα^{CS}/--^{SEA} | 156 (2.84) | 8.8 | 58.2 | 16 |  | F: 1.6 | 62 |

The Hb phenotype (Hb A, Hb A₂, Hb F, Hb E, Hb S) was investigated by cation-exchange chromatography (BioRad Variant II hemoglobin analyzer ® using the dual-kit elution system).
splenectomised patient
*MCV: mean cell volume
**MCH: mean corpuscular hemoglobin
^ΔThis patient was found to be heterozygous for an extended deletion removing from Hs 40 to 3' of alpha 1 gene By Multiplex Ligation PCR Analysis (P140B kit, MRC Holland, Amsterdam, the Netherlands)

REFERENCES

Bank A., AHSP: a novel hemoglobin helper. J Clin Invest. 2007 July; 117(7):1856-65.

Baudin-Creuza, V., Vasseur-Godbillon, C., Pato, C., Préhu, C., Wajcman, H., Marden, M. C, 2004. Transfer of human alpha to beta hemoglobin via its chaperon protein: evidence for a new state. J. Biol. Chem. 279, 36530-36533.

Baudin-Creuza V, Chauvierre C, Domingues E, Kiger L, Leclerc L, Vasseur C, Célier C, Marden M. C. 2008. Octamers and nanoparticles as hemoglobin based blood substitutes. BBA-Proteins and Proteomics. 1784, 1448-1453.

Domingues, E., Brillet, T., Vasseur, C., Agier, V., Marden, M. C., Baudin-Creuza, V. Construction of a new polycistronic vector for over-expression and rapid purification of human hemoglobin. Plasmid, 2009, 61, 71-77.

Gell, D., Kong, Y., Eaton, S. A., Weiss, M. J., Mackay, J. P., 2002. Biophysical characterization of the alpha-globin binding protein alpha-hemoglobin stabilizing protein. J. Biol. Chem. 277, 40602-40609.

Geraci, G., Parkhurst, L. J., and Gibson, Q. H., 1969. Preparation and properties of alpha- and beta-chains from human hemoglobin. J. Biol. Chem. 244, 4664-4667.

Feng L, Gell D A, Zhou S, Gu L, Kong Y, Li J, Hu M, Yan N, Lee C, Rich A M, Armstrong R S, Lay P A, Gow A J, Weiss M J, Mackay J P, Shi Y., 2004. Molecular mechanism of AHSP-mediated stabilization of alpha-hemoglobin. Cell. 119, 629-40.

Feng L, Zhou S, Gu L, Gell D A, Mackay J P, Weiss M J, Gow A J, Shi Y., 2005. Structure of oxidized α-haemoglobin bound to AHSP reveals a protective mechanism for haem. Nature, 435, 697-701.

Fessas, P., Loukopoulos, D., Kaltsoya, A., 1966. Peptide analysis of the inclusions of erythroid cells in beta-thalassemia. Biochim Biophys Acta. 1966, 124, 430-2.

Kim, H. C., Weierbach, R. G., Friedman, S., Schwartz, E., 1977, Blood. 49, 785-92.

Kihm, A. J., Kong, Y., Hong, W., Russel, J. E., Rouda, S., Adachi, K., Simon, M. C., Blobel, G. A., Weiss, M. J. 2002. An abundant erythroid protein that stabilizes free α-haemoglobin. Nature 417, 758-763.

Parkhurst, K. M., and Parkhurst, L. J. 1992. Rapid preparation of native alpha and beta chains of human hemoglobin. Int. J. Biochem. 24, 993-998.

Rose, C., Rossignol, J., Lambilliotte, A., Depret, S., Maboudou, P., Pissard S. 2009. A novel (ε,γ,δ,β) (0)-thalassemia deletion associated with an alpha globin gene triplication leading to a severe transfusion dependant foetal thalassemic syndrome. Haematologica, 94, 593-594.

Thein, S. L. 2005. Genetic modifiers of beta-thalassemia. Haematologica. 90, 649-60.

Weatherall, D. J. 2004. Thalassaemia: the long road from bedside to genome. Nat Rev Genet. 5, 625-31.

Weatherall, D. J., Clegg, J. B., Naughton, M. A. 1965. Globin synthesis in thalassaemia: an in vitro study. Nature. 208, 1061-1065.

Weatherall, D. J., and Clegg, J. B. The thalassemia syndromes (4$^{th}$ ed.) (2001) Oxford, Blackwell Scientific Publications Yu X, Kong Y, Dore L C, Abdulmalik O, Katein A M, Zhou S, Choi J K, Gell D, Mackay J P, Gow A J, Weiss M J. An erythroid chaperone that facilitates folding of alpha-globin subunits for hemoglobin synthesis. J Clin Invest. 2007 July; 117(7):1856-65.

The invention claimed is:

1. A method for monitoring a treatment against a hemoglobin disorder with an imbalance in the synthesis of hemoglobin chain in a subject in need thereof, said method comprising:

contacting blood samples obtained from said subject, before and after administration of said treatment to said subject, with Alpha-Hemoglobin Stabilizing Protein (AHSP) to bind free monomeric alpha hemoglobin (α-Hb), detecting and/or quantifying the presence of AHSP-bound free monomeric α-Hb in said blood samples, and correlating said amount of the AHSP-bound free monomeric α-Hb with monitoring of a treatment against said hemoglobin disorder in said subject, wherein said treatment is determined to be effective for use as treatment of said hemoglobin disorder in said subject when the amount of the AHSP-bound free monomeric α-Hb detected and/or quantified in said subject after administration of said treatment is decreased as compared to the amount of the AHSP-bound free monomeric α-Hb detected and/or quantified in said subject before administration of said treatment and wherein said treatment is determined to be ineffective for use as treatment of said hemoglobin disorder in said subject when the amount of the AHSP-bound free monomeric α-Hb detected and/or quantified in said subject after administration of said treatment is the same or increased as compared to the amount of the AHSP-bound free monomeric α-Hb detected and/or quantified in said subject before administration of said treatment.

2. The method according to claim 1, wherein the step of detecting and/or quantifying the AHSP-bound free monomeric α-Hb is carried out by photometry.

3. The method according to claim 1, wherein the step of detecting and/or quantifying the AHSP-bound free monomeric α-Hb is carried out by immunological detection.

4. The method according to claim 3, wherein the immunological detection of the AHSP-bound free monomeric α-Hb is carried out by using at least one antibody that binds specifically to α-Hb.

5. The method according to claim 3, wherein the immunological detection of the AHSP-bound free monomeric α-Hb is carried out by an enzyme immunoassay or enzyme-linked immunoassay (EIA or ELISA).

6. The method according to claim 3, wherein the immunological detection of the AHSP-bound free monomeric α-Hb is carried out by homogeneous time resolved fluorescence (HTRF).

7. The method according to claim 1, wherein the treatment against said haemoglobin disorder with an imbalance in the synthesis of hemoglobin chain is selected from the group consisting of treatment with iron, treatment with erythropoietin, treatment with cobalamin, and treatment with γ chain synthesis stimulating agent.

8. The method according to claim 1, wherein the hemoglobin-disorder with an imbalance in the synthesis of hemoglobin chain is selected from the group consisting of β-thalassemia, γ-thalassemia, syndromic thalassemia conditions, anemia, sickle cell disease, unstable Hb variants and hereditary persistence of fetal Hb.

9. The method according to claim 1, wherein the hemoglobin-disorder with an imbalance in the synthesis of hemoglobin chain is β-thalassemia.

10. The method according to claim 1, wherein the AHSP-bound free monomeric α-Hb is detected with a kit comprising:
   a solid support, and
   an α-Hb-specific binding partner coated to the solid support.

* * * * *